United States Patent [19]
Kinnersley et al.

[11] Patent Number: 5,350,735
[45] Date of Patent: Sep. 27, 1994

[54] COMPOSITION AND METHOD FOR ENHANCED FERTILIZER UPTAKE BY PLANTS

[75] Inventors: Alan M. Kinnersley, Knoxville, Tenn.; Larry P. Koskan, Orland Park, Ill.; David J. Strom, New Market, Tenn.; Abdul R. Y. Meah, Justice, Ill.

[73] Assignee: Donlar Corporation, Bedford Park, Ill.

[21] Appl. No.: 972,375

[22] Filed: Nov. 5, 1992

[51] Int. Cl.$^5$ .................. A01N 37/44; A01N 59/00
[52] U.S. Cl. ................... 504/147; 504/121; 504/125; 504/320
[58] Field of Search ............... 504/320, 143, 121, 123, 504/125, 147

[56] References Cited
U.S. PATENT DOCUMENTS

| | | | |
|---|---|---|---|
| 4,172,072 | 10/1979 | Ashmead | 260/115 |
| 4,799,953 | 1/1989 | Danzig et al. | 71/98 |
| 4,813,997 | 3/1989 | Kinnersley et al. | 71/66 |
| 4,839,461 | 6/1989 | Boehmke | 528/363 |
| 4,863,506 | 9/1989 | Young | 71/113 |
| 4,863,898 | 9/1989 | Ashmead et al. | 514/6 |
| 5,059,241 | 10/1991 | Young | 71/106 |

OTHER PUBLICATIONS

Kinnersley et al., Plant Growth Regulation 9:137-146 (1990).
Byrnes, Fertilizer Research 26:209-215 (1990).
Farm Chemicals Handbook, 1987, Meister Pub Co. Willoughby Ohio, p. B10.

*Primary Examiner*—Glennon H. Hollrah
*Assistant Examiner*—B. Bembenick
*Attorney, Agent, or Firm*—Olson & Hierl, Ltd.

[57] ABSTRACT

Water-soluble poly(organic acids) having a molecular size of more than 1,500 Daltons enhance fertilizer uptake and promote plant growth. Particularly suitable for this purpose are the poly(amino acids) such as poly(aspartic acid) and copolymers thereof.

20 Claims, 3 Drawing Sheets

CONTROL　　　　DGI - K1 - (10ppm)
FULL FERTILIZER　　FULL FERTILIZER

CONTROL　　　　DGI - K1 - (10ppm)
FULL FERTILIZER　　1/3 FERTILIZER

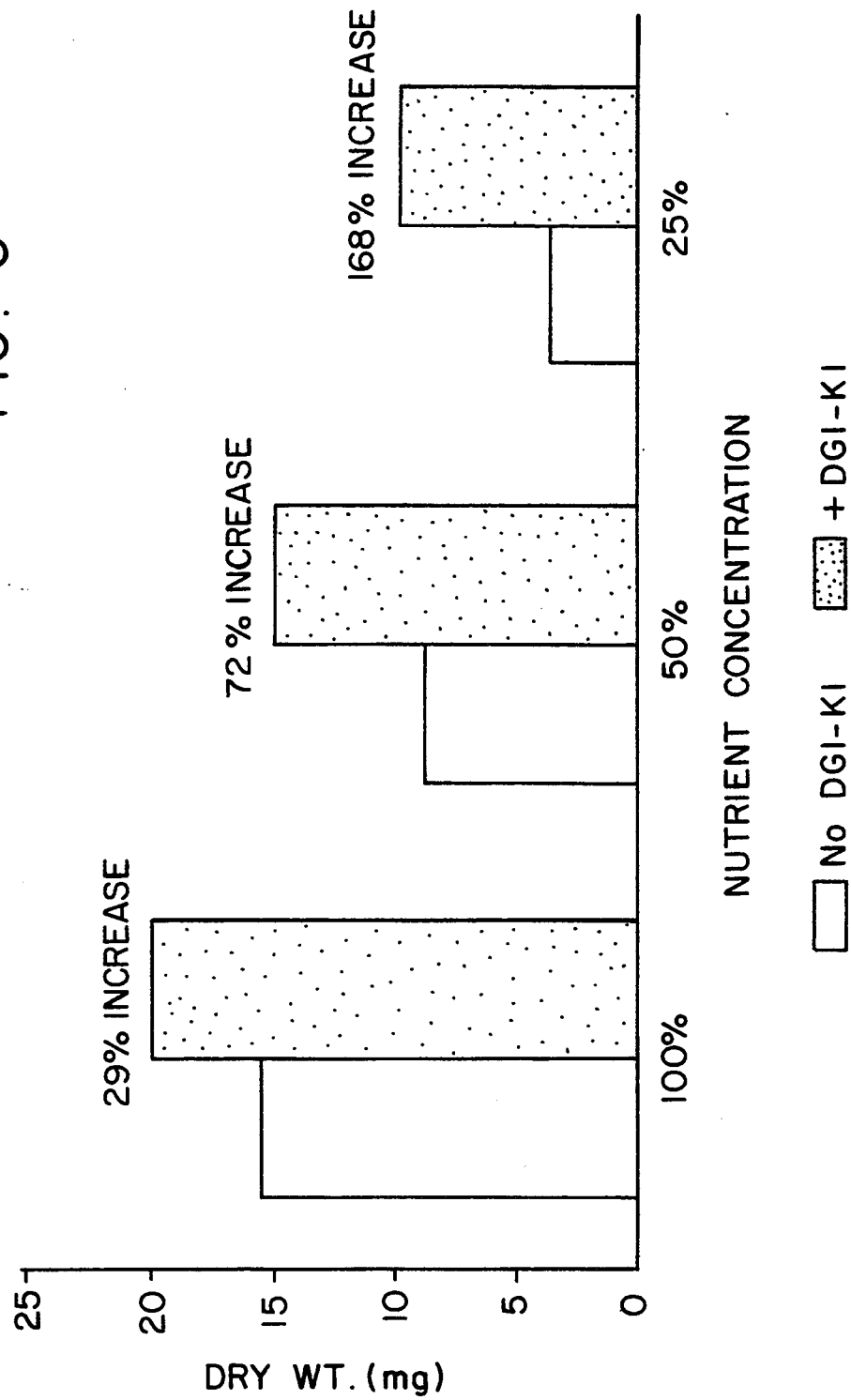

COMPOSITION AND METHOD FOR ENHANCED FERTILIZER UPTAKE BY PLANTS

TECHNICAL FIELD

This invention relates to the promotion of plant growth. More particularly, this invention relates to compositions and methods that facilitate the assimilation of nutrients by plants.

BACKGROUND OF THE INVENTION

Organic acids and oligomers thereof have been shown to promote plant growth. Typical such regulators of plant growth are described by Kinnersley et al., Plant Growth Regulation 9:137–146 (1990), which publication mentions the effects of lactic acid and relatively low molecular weight oligomers of lactic acid on plant growth. Similar description is found in U.S. Pat. No. 4,813,997 to Kinnersley et al. (oligomers of glycolic and/or L-lactic acid) and U.S. Pat. No. 4,799,957 to Danzig et al. (oligomers of thiolactic and thioglycolic acids). All of the forgoing approaches to plant growth enhancement appear to focus on chelation as a means for enhancing plant uptake of compounds vital to the growth of the plant, e.g., micronutrients such as calcium, magnesium, sulfur, manganese, zinc, copper, iron, boron, and the like.

A very common approach to the enhancement of plant growth has been, and continues to be, the use of fertilizers, natural as well as synthetic. The latter usually provide nitrogen in a plant-usable form, such as urea for example, and/or inorganic nitrates, phosphates, or the like compounds. While such fertilizers may be applied, more or less, at the convenience of the farmer, and may be applied as often as deemed desirable, the overuse of synthetic fertilizers is a major factor responsible for environmental problems such as eutrophication of ground water, nitrate pollution, phosphate pollution, and the like. An overview of the undesirable effects of nitrogen fertilizers is presented by Byrnes, Fertilizer Research 26:209–215 (1990).

To ameliorate the problems attendant to fertilizer overuse, it would be desirable to increase fertilizer efficiency. The present invention addresses these problems, and provides compositions and methods for enhancing the fertilizer uptake efficiency of plants.

SUMMARY OF THE INVENTION

Enhanced plant productivity and growth as manifested by growth rate, increased biomass, increased yield, increased rate of root formation, increased chlorophyll concentration, and the like indicia, is achieved at reduced fertilizer levels by making available to the plant a mixture of the fertilizer and a poly(organic acid) that is water soluble and not absorbed into the plant, i.e., having a molecular size larger than 1,500 Daltons. Such poly ( organic acids ) are non-aromatic polymers that have at least about 15 repeating organic acid units or mers in the polymer chain. Preferred are non-chelating poly(organic acids).

Particularly preferred for the present purposes are polymers such as a poly(amino acid), e.g., poly(aspartic acid), alone or in combination with a poly(carboxylic acid), e.g., a poly(lactic acid), and the like.

BRIEF DESCRIPTION OF THE DRAWINGS

In the drawings, there are shown photographic reproductions of corn plants treated in a particular manner alongside a control corn plant. In each case a yardstick (36 inches) is shown positioned between the photographed plants to indicate scale. In particular.

FIG. 5 is a graphical representation of growth enhancement with poly(aspartic acid) as reported in Example 15, below.

DETAILED DESCRIPTION OF PREFERRED EMBODIMENTS

Figure 1:
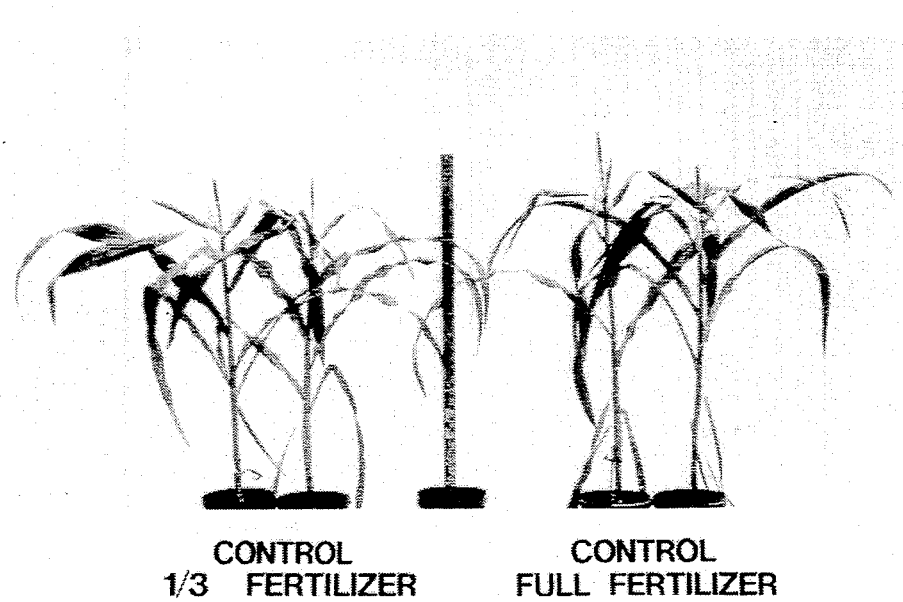
FIG. 1 shows corn plants 40 days after planting, and treated with one-third of the recommended fertilizer dosage alongside a corn plant treated with the recommended dosage for the same fertilizer.

The present invention, in its various aspects, is predicated on the discovery that polymeric organic acids that are too large to enter a plant nevertheless can promote plant growth when made available to the plant in conjunction with a fertilizer that supplies the necessary nutrients. A more efficient utilization of such nutrients can be realized in the presence of the polymeric organic acid inasmuch as relatively lower fertilizer dosages can be relied upon to provide the requisite nutrients to the plant.

In general, the polymeric organic acids can be made available to the plant as fertilizer solutions containing at least about 10 parts per billion (ppb) by weight, preferably about 0.1 to about 1,000 parts per million (ppm) by weight, more preferably about 1 to about 500 ppm by weight, of the polymeric organic acid in the solution. Such solutions can be applied to the soil surrounding the plant so as to contact the plant's root system, can be applied to the plant's foliage utilizing usual foliar feeding techniques, can be introduced into hydroponic gardening or farming systems, and in any other convenient manner. Solutions containing the polymeric organic acid can be sprayed or otherwise applied to contact the roots, stems, or leaves of the plants whose growth and/or development is to be enhanced, as well as to the seeds of these plants, in a growth promoting amount as is discussed in greater detail hereinbelow. Solutions containing the polymeric organic acid are also useful to promote effective plant growth under growth limiting conditions, e.g., in soil that contains salts in concentrations normally toxic to plants, soil depleted in certain nutrients, etc.

The polymeric organic acids, to be suitable for the practice of the present invention, must be water soluble, non-aromatic, and must have a molecular size sufficiently large to preclude absorption into the plant's own system. To that end, the non-aromatic polymeric organic acids deemed suitable for the present purposes, While hydrophilic, have a molecular size larger than 1,500 Daltons and have at least about 15 repeating organic acid units (residues), or mers, in the linear polymer chain that constitutes the polymeric acid. Such linear polymer chains can be cross-linked, if desired, but only to a degree that does not materially affect the water solubility of the polymeric moiety. Polymeric organic acids having a molecular size in excess of about 100,000 Daltons usually do not exhibit adequate solubility in water for the present purposes, thus for present purposes a polymeric organic acid molecular size not larger than about 100,000 Daltons is preferred. Particularly preferred molecular size is in the range of about 2,000 to about 30,000 Daltons.

Illustrative are polymeric organic acids, with or without carboxylic acid, thiocarboxylic acid, imidocarboxy, and/or amino side chains, such as, for example, poly(acrylic acid), poly(maleic acid), poly(lysine), poly(glutamic acid), poly(aspartic acid), poly(glycine), poly(cysteine), poly(cysteine/glutamic acid), mixtures of the foregoing, and the like. Block or random copolymers or terpolymers of several organic acids are also within the purview of the present invention as the polymeric acid component thereof. For example, the utilized polymeric acid component can be a block copolymer of aspartic acid residues and L-lactic acid residues, a random copolymer of aspartic acid residues and glycolic acid residues, a conjugated protein constituted by amino acid residue chains interconnected by one or more polycarboxylic acid residues, a copolymer of acrylic acid and acrylamide, and the like.

Polymers of organic acids are commercially available. In addition, such polymeric acids, especially poly(amino acids), can be made, inter alia, by thermal condensation methods. See, for example, U.S. Pat. No. 5,057,597 to Koskan, Little et al., American Chemical Society 97:263-279 (1991), and U.S. Pat. No. 4,696,981 to Harada et al.

The starting materials for the polymerization, i.e., the organic acids, can exist as optical isomers, depending upon their respective structures, and can be polymerized either as a racemic mixture or as segregated optical isomers.

A racemic mixture is an equal molar mixture of the two possible optical isomers—the levorotatory and dextrorotatory isomers. Levorotatory (l) isomers are isomers of an optically active compound which rotate a beam of polarized light to the left; the dextrorotatory (d) isomers are isomers of the same compound which rotate a beam of polarized light to the right. Another convention employed to define the configurational relationships of dissimilar functional groups bonded to an asymmetric carbon atom, the so-called Fischer Method, is based on the geometric arrangement of functional groups relative to each other rather than on the direction (left or right) in which a standard solution of the compound rotates a beam of polarized light. The Fischer Method is well known in the art, and is discussed in more detail in Fieser & Fieser, *Introduction to Organic Chemistry*, D. C. Heath and Co., Boston, Mass., (1957) at pages 209-215. The Fischer Method designations are used herein.

In accordance with the Fischer Method, any compound which contains an asymmetric carbon atom of the same configuration as the asymmetric carbon in the arbitrary standard, dextrorotatory glyceraldehyde, is classified in the D series, while compounds in which the asymmetric carbon atom has the opposite configuration are classified in the L series. Although the Fischer D and L classifications do not correlate with dextro- (d) and levorotatory (l) optical activity for all compounds, those classifications can be used in combination with the optical activity classifications d and l to define both the geometric arrangement and specific optical activity of any optically active isomer. Thus, the L-isomer of lactic acid, which is dextrorotatory, is defined as L-(d)-lactic acid, and the D isomer is defined as D-(l)-lactic acid. However, both of these characteristics of relatively simple compounds can be adequately defined by reference to only one classification system. For example, L-lactic acid is known to be dextrorotatory and l-lactic acid is known to have the D configuration according to Fischer. For this reason, the D and L isomers of lactic acid and other relatively simple organic acids are usually identified only by the D and L designations, and without explicit reference to their optical activity.

For organic acids that exhibit optical activity, the polymers and copolymers of the L-isomers are preferred. However, racemic mixtures as well as polymers and copolymers of the D-isomers can be utilized for the present purposes.

In some instances either the L-form or the D-form may exhibit greater biological activity vis-a-vis plant growth promotion. In such instances the more active form is, of course, the preferred form.

Hydrophobic polymeric organic acids such as poly(alanine) and poly(hydroxybutyric acid) are not suitable.

Particularly well suited for the practice of the present invention are the non-chelating poly(organic acids) such as poly(acrylic acid) and the like, as well as the poly(amino acids) such as poly(aspartic acid) having a molecular size in the range of about 3,000 to about 28,000 Daltons, poly(glutamic acid) having a molecular size in the range of about 4,000 to about 14,000 Daltons, poly(glycine) having a molecular size in the range of more than 1,500 to about 7,000 Daltons, and poly(lysine) having a molecular size in the range of about 2,000 to about 7,000 Daltons.

The term "chelate," as used herein in its various forms, refers to a complex formed by a polydentate ligand, i.e., a ligand that supplies more then one pair of electrons to a cation. See, for example, Masterson et al., *Chemical Principles*, 6th ed., Saunders College Publishing Co., Philadelphia, Pa. (1985), p. 635.

Similarly, the term "chelating agent," as used herein in its various forms, refers to a ligand that possesses at least two pairs of unshared electrons which pairs are far enough removed from one another to give a ring structure with a stable geometry. Ibid, p. 638.

The presently contemplated poly(organic acids) are not chelating agents, and as such do not form chelates with the plant nutrients.

The fertilizer that can be utilized in conjunction with the aforesaid poly(organic acids) can be any chemical moiety, natural or synthetic, that serves as a source of macro nutrients (N, P, K) and/or micro nutrients (Ca, Mg, S, Zn, Fe, Mn, B, Co, Mo, Cu, Ni) for the plant under consideration.

There are many uses and applications for the present inventions in its various aspects. Illustrative are uses in agriculture, gardening, horticulture, hydroponics, forestry, land reclamation (e.g., landfills, soils with relatively high salt concentration, etc.), and the like.

Suitable dosage rates for soil treatment with the polymeric organic acid component of the present invention so as to provide a growth promoting amount of the polymeric acid to the plant are in the overall range of about 2 to about 500 ounces of the polymeric organic acid per acre. Crops with an abundance of foliage, such as wood crops, grain crops, cotton, etc., usually are treated at dosage rates in an intermediate range, i.e., about 25 to about 250 ounces per acre. Relatively lower dosage rates within the foregoing overall range, i.e., about 2 to about 25 ounces per acre, usually are sufficient for agricultural row crops, flowering nursery crops, and the like.

The polymeric organic acid component is made available to the plant together with the fertilizer component. Solid as well as liquid dosage forms can be utilized for this purpose, e.g., aqueous solutions, solid soil conditioning substances such as particulate clays bearing the polymeric organic acid commingled with the fertilizer component, solid particulate admixtures of fertilizer and polymeric organic acid, and the like.

The present invention is further illustrated by the following examples.

EXAMPLE 1: Effect of Poly(Aspartic Acid) Under Growth Limiting Conditions

Duckweed (*Lemna minor* L.) was grown in tap water containing as nutrient media a solution of Peters ™ 20-20-20 fertilizer[1] (3 g/1.2L) and a ¼-strength solution (750 mg/1.2L) with and without 50 ppm by weight poly(aspartic acid) (PA). The nutrient media were adjusted to a pH value of about 6.0. The molecular size of the PA was about 3,000 to 5,000 Daltons (about 22 to about 40 repeating units).

A single duckweed plant at the three-frond stage was placed in each flask. The flasks were then incubated under continuous light (500 lux) at 28°±2° C. for 21 days.

| [1]Total Nitrogen (N) | 20% |
|---|---|
| 3.90% Ammoniacal Nitrogen | |
| 6.15% Nitrate Nitrogen | |
| 9.95% Urea Nitrogen | |
| Available Phosphoric Acid ($P_2O_5$) | 20% |
| Soluble Potash ($K_2O$) | 20% |
| Derived from: Ammonium, Phosphate, Potassium Nitrate, Urea. | |
| Commercially available from Grace-Sierra Horticultural Products Company, 1001 Yosemite Drive, Milpitas, CA 95035. | |

After 21 days the plants were harvested, oven-dried, and weighed. Results show that nutrient reduction by 75% reduced plant weight by 74%, and that (A) no significant reduction in plant growth was found when PA was present in the medium with 25% nutrients and (B) plant growth was enhanced when PA was present in the medium with 100% nutrients. The results are presented in Table I, below. All reported values represent 3 to 5 replicates.

TABLE I

| | Results | | | |
|---|---|---|---|---|
| | Plant dry wt.-milligrams (mg) | | | |
| Treatment | Expt. A | Expt. B | Average | % Change |
| 100% Nutrients | 16.5 | 17.7 | 16.6 | 0 |
| 100% Nutrients + PA | 21.3 | 22.2 | 21.7 | 31 |
| 25% Nutrients | 4.7 | 4.0 | 4.4 | −74 |
| 25% Nutrients + PA | 15.2 | 16.7 | 16.0 | 0 |

EXAMPLE 2: Effect of Poly(Aspartic Acid) on Biomass

The procedure described in Example 1, above, was followed except that a chemically defined nutrient medium having the composition described in U.S. Pat. No. 4,813,997 to Kinnersley et al. (Nickell's medium with Fe present as $Fe^{2+}$ chelated with EDTA) was used. The plants were grown in five replicate flasks, harvested after 21 days, and the combined dry weight of the harvested plants was determined. The content of potassium and phosphorus in the plants and in the spent media was determined as well. The observed results are presented in Table II, below.

TABLE II

| | Changes in Biomass | | |
|---|---|---|---|
| | | Amount of Mineral ($\mu g$), control/with PA | |
| Treatment | Plant Biomass (mg) | Spent Media | Plants |
| 100% Nutrients/ 100% Nutrients + 50 ppm PA | 94.4/90.9 | | |
| Potassium (K) | | 11,610/11,740 | 1540/1530 |
| Phosphorus (P) | | 1170/1140 | 250/280 |
| 25% Nutrients/ 25% Nutrients + 50 ppm PA | 67.3/89.3 | | |
| K | | 2420/1770 | 990/1530 |
| P | | 334/322 | 125/173 |
| 12.5% Nutrients/ 12.5% Nutrients + 50 ppm PA | 54.1/62.7 | | |
| K | | 955/718 | 769/942 |
| P | | 190/192 | 89/111 |

The above results show that nutrient concentration reduced by 75% caused a 29% reduction in plant biomass (94.4–67.3) and a 36% reduction in the potassium content of plants (1540–990). However, in the same treatments containing poly(aspartic acid) the plant biomass was barely reduced (90.9–89.3), and the potassium content was unchanged. Analysis of the spent media showed much less potassium in the media containing PA. This data also indicate that the polymers had increased the uptake of potassium into plants.

The above results also show a remarkably good correlation between potassium content and plant-biomass as can be seen in Table III, below:

TABLE III

| | Correlation Between Potassium Content and Biomass | | | |
|---|---|---|---|---|
| | Nutrients | | Nutrients + PA | |
| Nutrient Amount | Biomass (mg) | K (mg) | Biomass (mg) | K (mg) |
| 100% | 94.4 | 1.54 | 90.9 | 1.53 |
| 25% | 67.3 | 0.99 | 89.3 | 1.53 |
| 12.5% | 54.1 | 0.77 | 62.7 | 0.94 |

Potassium is the most important metal needed for plant growth, and is the principal metal component of most fertilizers. However, heretofore no agent was known able to simultaneously increase the growth and potassium content of plants.

EXAMPLE 3: Plant Content of Nutrients

The content of other nutrients in plants from the full strength and ¼-strength treatments described in Example 2, above, was determined. The observed results are set forth in Table IV, below.

TABLE IV

Plant Nutrient Content

| Element | Amount, micrograms (µg) | | |
|---|---|---|---|
| | 100% Nutrients | 25% Nutrients | 25% Nutrients + 50 ppm PA |
| Zn | 9.2 | 2.6 | 3.7 |
| Mg | 70 | 43 | 49 |
| Fe | 2.5 | 1.0 | 5.9 |
| Ca | 340 | 172 | 243 |
| Cu | 3.9 | 3.7 | 3.2 |
| Mn | 4.1 | 1.1 | 1.1 |
| Biomass, mg | 94.4 | 67.3 | 89.3 |

These results show that the content of most other minerals needed for plant growth was also greatly increased by the presence of PA. Particularly noteworthy is the substantial increase in the iron content at reduced nutrient level.

EXAMPLE 4: Effect of Poly(Aspartic Acid) on Corn Plants

White corn (*Zea mays* L.) seed (5145 Truckers Favorite; George W. Park Seed Co., Greenwood, S.C.) was planted in 8-cm black round pots with Fafard 3B potting soil. Each pot was given 0.3 g, 0.15 g, or 0.075 g of Peters TM 20-20-20 fertilizer. Five pots representing each treatment were kept as controls, five pots were given 50 ml of 5 ppm aqueous PA solution, and five pots 50 ml of a 500 ppm aqueous PA solution. After six weeks the plants were harvested, and the fresh weight and nitrogen content of the harvested plants was determined. The observed results are reported in Table V, below.

TABLE V

Effect of Poly(Aspartic Acid) on Corn Plants

| Treatment | Harvested Plants | |
|---|---|---|
| | Fresh wt., g | Average N content, mg |
| 100% nutrients | 45.8 | 67.6 |
| 100% nutrients + 5 ppm PA | 46.5 | 75.7 |
| 100% nutrients + 500 ppm PA | 50.2 | 73.2 |
| 50% nutrients | 34.7 | 40.5 |
| 50% nutrients + 5 ppm PA | 45.6 | 57.6 |
| 50% nutrients + 500 ppm PA | 38.6 | 49.6 |
| 25% nutrients | 24.1 | 29.6 |
| 25% nutrients + 5 ppm PA | 31.7 | 36.2 |
| 25% nutrients + 500 ppm PA | 38.3 | 47.8 |

Above results show that PA enables plants to be grown with a 50% reduction in nutrients without showing any reduction in growth. Simultaneously with increasing the corn biomass, PA also increased the nitrogen content of the corn. Plants grown with 25% nutrients and 500 ppm PA contained more nitrogen than plants grown with 50% nutrients that were given twice the amount of nitrogen.

EXAMPLE 5: Effect of Poly(Lysine) on Corn Plants

Twenty white corn plants (5145 Truckers Favorite) were grown in a greenhouse in ten 8 cm diameter round pots with Fafard 3B potting soil. Each pot was given 50 ml of a solution containing 15,000 ppm of Peters TM 20-20-20 fertilizer. Half the pots were additionally given weekly 50-ml treatments of 1 ppm poly(lysine) (PL; molecular size: about 1,500 Daltons) for four weeks. Plants were harvested after five weeks, and dry weights thereof as well as nitrogen content were determined. The observed results are reported in Table VI, below.

TABLE VI

Dry Weight and Nitrogen Content

| Treatment | Harvested Plants | |
|---|---|---|
| | Biomass | Average N content per plant, mg |
| Control | 5.2 | 18.5 |
| Control + 1 ppm PL | 6.6 | 24.5 |

The foregoing results show that PL increased corn biomass 27% and increased the nitrogen content of the corn plants by 32%.

EXAMPLE 6: Treatment of Bean Plants with Poly(Aspartic Acid)

Garden beans (Mayo's Red Peanut Bush) were grown in the greenhouse in gallon pots filled with Fafard 3B potting soil. Ten pots were given 50 ml of a 7,500 ppm solution of Peters TM 20-20-20 fertilizer. Twenty pots were given 50 ml of a 2,500 ppm Peters TM fertilizer solution, and 10 of these pots were also given four weekly treatments of 50 ml aliquots of a 1 ppm solution of PA in water. When the bean plants flowered, they were taken outside for insect pollination. The beans that grew were harvested. The number and weight of beans on each plant was then determined. Results in Table VII, below, show that PA increased reproductive growth resulting in more beans and a greater weight yield of beans from each plant. The doubling in bean yield in the ⅓ fertilizer treatment with PA, compared to the fertilizer alone, was statistically significant with Duncan's multiple range test.

TABLE VII

Yield of Beans

| Treatment | Harvested Beans | |
|---|---|---|
| | Average # of Beans/Plant | Average Fresh Weight of Beans/Plant, g |
| Full fertilizer | 4.1 | 4.51 |
| ⅓ fertilizer | 3.4 | 1.8 |
| ⅓ fertilizer + 1 ppm PA | 8.2 | 7.99 |

EXAMPLE 7: Effect of Poly(Aspartic Acid) on Rapeseed

A fast growing variety of rapeseed (*Brasica rapus*) was obtained from the Crucifer Genetics Cooperative at the University of Wisconsin. This variety was grown in 9-cm pots in a greenhouse. Pots were given 50 ml of a full strength solution of Peters TM 20-20-20 fertilizer (7,500 ppm) in water, or the same volume of a 3,750 ppm solution in water. Some of the pots were given 50 ml of a 2 or 20 ppm solution of PA in water as a single treatment or once a week for four weeks. Plants were pollinated by hand when they flowered. Mature seed pots were harvested. The observed results are reported in Table VIII, below.

TABLE VIII

Rapeseed Harvest

| Treatment | Harvested Rapeseed | |
|---|---|---|
| | Average # Pods per Plant | Average Dry Weight of Pods per Plant, mg |
| Full fertilizer | 3.8 | 202 |
| 50% fertilizer | 2.9 | 174 |

TABLE VIII-continued

| | Rapeseed Harvest | |
|---|---|---|
| | Harvested Rapeseed | |
| Treatment | Average # Pods per Plant | Average Dry Weight of Pods per Plant, mg |
| 50% fertilizer + 2 ppm PA (S) | 4.8 | 283 |
| 50% fertilizer + 2 ppm PA (M) | 4.8 | 267 |
| 50% fertilizer + 20 ppm PA (S) | 5.2 | 290 |
| 50% fertilizer + 20 ppm PA (M) | 3.4 | 179 |
| Full fertilizer + 2 ppm PA (S) | 5.0 | 271 |

(S) = single application
(M) = multiple application

The above results show that average grain yield was higher in plants given PA than in plants receiving fertilizer alone. This was true whether plants were given multiple or single applications of PA. PA increased grain yield in plants given both full and ½ strength fertilizer. In many plants yield was higher for plants given ½ strength fertilizer+PA than in plants receiving full fertilizer alone.

EXAMPLE 8: Effect of Poly(Aspartic Acid) on Leaf Uptake of Calcium and Boron Discs were cut from Navel orange leaves and floated for 1 hour, 3 hours, and 4 hours in an aqueous solution of calcium boron (SORBA SPRAY® CaB fertilizer available from Leffingwell Chemical Company) diluted 1:400 with water. Replicate discs from the same leaves were floated for the same time periods in solutions of SORBA SPRAY® CaB fertilizer containing 2 and 10 ppm PA. At the appropriate time discs were taken out, thoroughly washed, oven-dried, and analyzed for calcium and boron content. The results are set forth in Table IX, below.

TABLE IX

| | Uptake of Calcium and Boron | | | | | |
|---|---|---|---|---|---|---|
| | Content of Ca (% Dry Weight) and B (ppm) in Leaf Discs | | | | | |
| | 1 h | | 3 h | | 4 h | |
| Treatment | Ca | B | Ca | B | Ca | B |
| Sorba Spray ® CaB | 4.86 | 61 | 4.48 | 67 | 4.37 | 78 |
| Sorba Spray ® CaB + 2 ppm PA | 4.42 | 64 | 5.04 | 72 | 5.36 | 84 |
| Sorba Spray ® CaB + 10 ppm PA | 5.58 | 75 | 5.88 | 75 | 5.96 | 95 |

In treatments with 10 ppm PA in diluted Sorba Spray ® CaB fertilizer the leaf discs contained an average of 5.8 Ca and 82 ppm B, compared to 4.6 Ca and 69 ppm B in diluted Sorba Spray ® CaB fertilizer alone. PA therefore increased uptake of Ca and B into leaf tissue by 26% and 19% respectively.

EXAMPLE 9: Effect of Poly(Aspartic Acid) on Leaf Uptake of Iron

A procedure similar to that of Example 8 except with maple leaves var. Red Sunset was used. Leaf discs were floated in solutions of SORBA SPRAY® Fe fertilizer with or without different amounts of PA present. Leaf discs were treated for 3 hours then washed, dried, and analyzed for Fe content. The results are compiled in Table X, below.

TABLE X

| | Uptake of Iron | |
|---|---|---|
| | Dried Maple Leaves | |
| Treatment | Fe content - ppm | % Change |
| No treatment | 101 | 0 |
| Sorba Spray ® Fe | 863 | 754 |
| Sorba Spray ® Fe + PA 2 ppm | 884 | 775 |
| Sorba Spray ® Fe + PA 10 ppm | 933 | 823 |
| Sorba Spray ® Fe + PA 20 ppm | 1000 | 890 |
| Sorba Spray ® Fe + PA 50 ppm | 1106 | 995 |

The above results show that although the Sorba Spray® fertilizer increased Fe uptake into maple leaves, the solutions containing PA increased uptake even more. Leaves treated with Sorba Spray® fertilizer+50 ppm PA contained 28% more iron than those treated with Sorba Spray® fertilizer alone.

EXAMPLE 10: Enhanced Fertilizer Efficiency in Corn Plants

Figure 2:
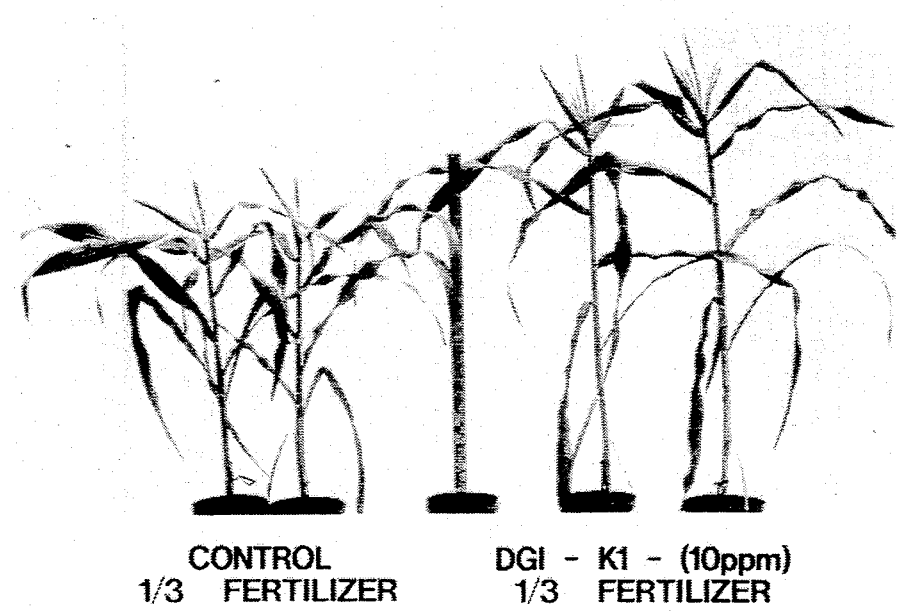
FIG. 2 shows a corn plant 40 days after planting, one treated with one third of the recommended fertilizer dosage alongside a corn plant similarly treated with the same fertilizer but also with 10 parts per million by weight of poly(aspartic acid)
Figure 3:
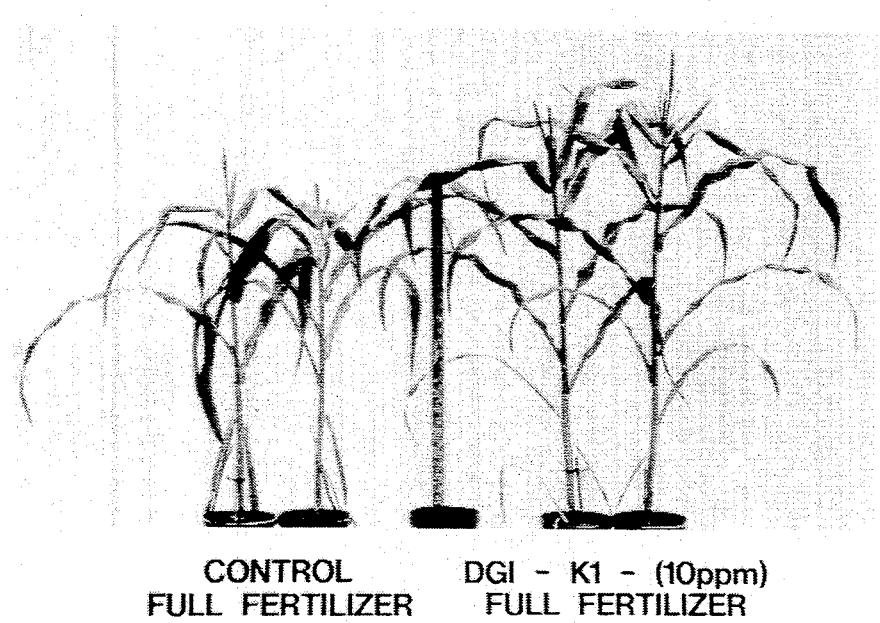
FIG. 3 shows corn plants 40 days after planting, both treated with the recommended fertilizer dosage and one plant also with 10 parts per million by weight of poly(aspartic acid)
Figure 4:
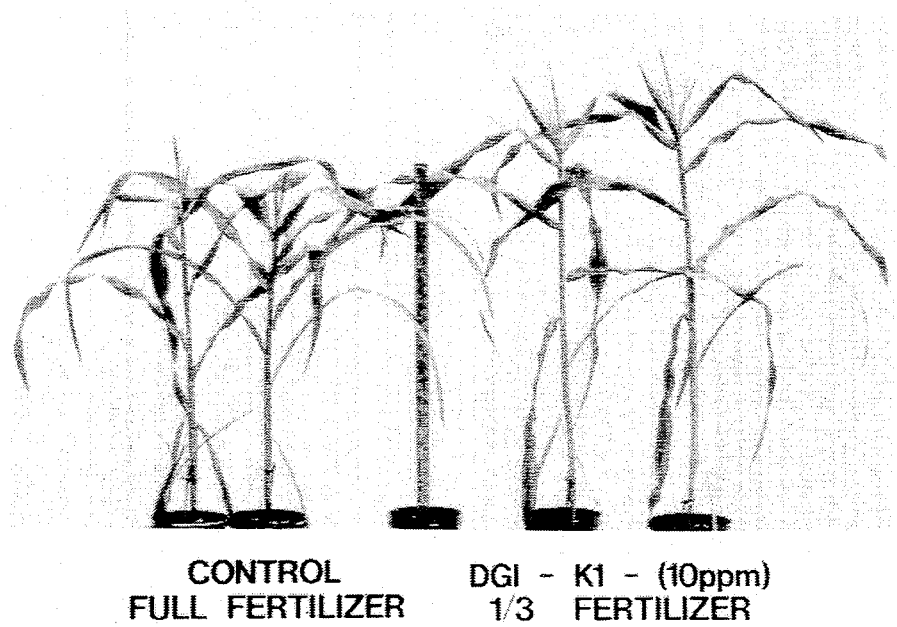
FIG. 4 shows corn plants 40 days after planting, one treated with the recommended fertilizer dosage and the other with one-third of the recommended fertilizer dosage but also with 10 parts per million by weight of poly(aspartic acid)

White corn (Early Sunglow; George W. Park Seed Co., Greenwood, S.C.) was grown in a greenhouse in one-gallon pots filled with Fafard 3B potting soil. To each pot was added Peters TM 20-20-20 fertilizer in an amount representing a full dose of nutrients or a ⅓ dose of nutrients. A portion of the pots so treated also received an aqueous solution of PA (50 ml; 10 ppm by weight of PA [Code DGI-K1] having a molecular size of about 3,000–5,000 Daltons). The growth rates of the white corn plants in these pots were monitored, and representative plants were photographed 40 days after planting. These photographs are depicted in FIGS. 1 through 4.

The foregoing FIGURES show that the availability of poly(aspartic acid) to the plant enhances plant growth at full nutrient level as well as at a reduced nutrient level.

EXAMPLE 11: Protection by Poly(Amino Acids) Against $Cu^{2+}$ Toxicity

A procedure similar to that described in Example 1 was followed, except that the growth medium contained Rapid Gro TM fertilizer[2] (2.5 g/1.2L) with and without 20 ppm by weight of $CuSO_4.5H_2O$. The pH of the medium was adjusted to 6.0. Except for the controls, the growth media contained poly(aspartic acid) (molecular size: about 3,000–5,000 Daltons) or a copolymer of cysteine and glutamic acid (molecular size: 1,500+ Daltons) or a terpolymer of cysteine, glutamic acid, and aspartic acid (molecular size: 1,500+ Daltons). Duckweed plants were harvested after 21 days of growth. The results are shown in Table XI, below.

| [2]Total Nitrogen (N) | 20% |
|---|---|
| 5.2% Ammoniacal Nitrogen | |
| 6.1% Nitrate Nitrogen | |
| 8.7% Urea Nitrogen | |
| Available Phosphoric Acid ($P_2O_5$) | 20% |
| Soluble Potash ($K_2O$) | 20% |
| Boron (B) | 0.02% |
| Copper (Cu) | 0.05% |
| 0.05% Chelated Copper | |
| Iron (Fe) | 0.10% |
| 0.10% Chelated Iron | |
| Magnesium (Mn) | 0.05% |
| 0.05% Chelated Magnesium | |
| Zinc (Zn) | 0.05% |
| 0.05% Chelated Zinc | |
| Primary nutrients from Urea, Ammonium | |

-continued

| |
|---|
| Phosphate and Potassium Nitrate, Micronutrients from Boric Oxide, Iron, Copper, Manganese and Zinc EDTA. Potential acidity equivalent to 600 lbs. calcium carbonate per ton. |

TABLE XI

| | Weight of Plants |
|---|---|
| Treatment | Plant Mean Dry Wt., mg |
| Control | 22.3 |
| $Cu^{2+}$ 20 ppm | 4.0 |
| $Cu^{2+}$ 20 ppm + 10 ppm PA | 5.7 |
| $Cu^{2+}$ 20 ppm + 20 ppm PA | 11.7 |
| $Cu^{2+}$ 20 ppm + 10 ppm copolymer | 10.0 |
| $Cu^{2+}$ 20 ppm + 20 ppm copolymer | 10.7 |
| $Cu^{2+}$ 20 ppm + 10 ppm terpolymer | 12.7 |
| $Cu^{2+}$ 20 ppm + 10 ppm terpolymer | 14.7 |

Results show that the above poly(amino acids) increased plant growth over that of plants with $Cu^{2+}$ alone, i.e., the polymers provided some protection against stress induced by $Cu^{2+}$ toxicity. The copolymer and terpolymer were significantly more effective than PA, especially at lower concentrations of the polymers, to reduce such stress.

EXAMPLE 12: Protection by Poly(Aspartic Acid) Against $Al^{3+}$ Toxicity

The procedure described in Example 11 was followed, except that the growth media contained 1000 μM $Al^{3+}$ added as $AlCl_3.6H_2O$. The media was adjusted to pH 6.0. Duckweed plants were harvested after 17 days growth. The results are presented in Table XII, below.

TABLE XII

| | Weight of Plants | |
|---|---|---|
| Treatment | Plant Mean Dry Wt., mg | % of Control |
| Control | 8 | 100 |
| $Al^{3+}$ | 3 | 37.5 |
| $Al^{3+}$ + PA 10 ppm | 2.7 | 34 |
| $Al^{3+}$ + PA 20 ppm | 4.7 | 59 |
| $Al^{3+}$ + PA 40 ppm | 5.3 | 66 |
| $Al^{3+}$ + copolymer 10 ppm | 6.7 | 84 |
| $Al^{3+}$ + copolymer 20 ppm | 12.7 | 159 |
| $Al^{3+}$ + terpolymer 10 ppm | 9.0 | 112 |
| $Al^{3+}$ + terpolymer 20 ppm | 13.5 | 169 |
| $Al^{3+}$ + terpolymer 40 ppm | 17.3 | 216 |

The above results show that poly(aspartic acid) in concentrations as low as 20 ppm and 40 ppm by weight provided protection against stress induced by $Al^{3+}$ toxicity. The copolymer and terpolymer were especially effective, and increased plant growth more than that of control plants without $Al^{3+}$ toxicity present in the growth medium.

EXAMPLE 13: Environmental Stability of Poly(Aspartic Acid)

A fertilizer solution was made by adding Peters TM 20-20-20 fertilizer (375 mg) to tap water (150 ml). The solution was divided into three aliquots. One 50-ml aliquot was maintained as a control. To another aliquot was added 1,000 ppm of poly(aspartic acid), and 1000 ppm of lactic acid oligomer containing less than ten lactic acid residues and obtained by thermal condensation of 88% L-lactic acid by heating at 70° C. for 4 hours followed by heating under vacuum at 100° C. for 4 hours was added to the last 50-ml aliquot. Solutions of all three aliquots were adjusted to pH 6.0.

The turbidity of the samples were measured every day to ascertain the extent of microbial growth in each sample. Within a few days the solution containing the lactic acid oligomer had become milky, indicating microbial contamination. The sample containing poly(aspartic acid) remained substantially clear, even after 7 days. The observations are compiled in Table XIII, below.

TABLE XIII

| | Turbidity Measurements | | | | |
|---|---|---|---|---|---|
| | Days | | | | |
| | 1 | 2 | 3 | 4 | 7 |
| Control | 0 | 0 | 0 | 0 | 0 |
| Poly(Aspartic Acid) | −0.04 | +0.25 | +0.26 | +0.40 | +0.95 |
| Lactic Acid Oligomer | −0.11 | +2.20 | +3.45 | +16.5 | +382.0 |

Results indicate that poly(aspartic acid) has a relatively longer life in the environment.

EXAMPLE 14: Nutrient Composition for Hydroponic Growing

An illustrative aqueous composition embodying the present invention and well suited for hydroponic farming is set forth in Table XIV, below.

TABLE XIV

| Hydroponic Growing Medium | |
|---|---|
| Nutrients, ppm by weight | |
| Nitrogen as N | 50 |
| Phosphorus as P | 48 |
| Potassium as K | 210 |
| Magnesium as Mg | 30 |
| Sulfates as $SO_4$ | 117 |
| Sodium as Na | 3.619 |
| Chlorides as Cl | 0.040 |
| Iron as Fe | 3.000 |
| Zinc as Zn | .150 |
| Copper as Cu | .150 |
| Boron as B | .500 |
| Manganese as Mn | .500 |
| Molybdenum as Mo | .100 |
| Water, q.s. | |

EXAMPLE 15: Effect of Poly(Aspartic Acid) Under Growth Limiting Conditions

Duckweed plants were grown in tap water under conditions described in Example 1, above, and containing as nutrient media a solution of Peters TM 20-20-20 fertilizer at full strength (100% nutrients), half-strength (50% nutrients), and one-quarter strength (25% nutrients), with and without 50 ppm poly(aspartic acid) (Code DGI-K1; molecular size: 3,000–5,000 Daltons).

The plants were harvested, oven-dried, and weighed after 21 days. The averaged plant dry weight is reported in Table XV, below. All reported values represent 12 to 20 replicates.

TABLE XV

| Treatment | Results Average Plant Dry Wt.-milligrams (mg) |
| --- | --- |
| 100% Nutrients | 15.5 |
| 100% Nutrients + PA | 20.0 |
| 50% Nutrients | 8.8 |
| 25% Nutrients | 3.7 |
| 25% Nutrients + PA | 9.9 |

The foregoing results are depicted graphically in FIG. 5. These results show that the addition of PA permits a decrease in nutrient level by about 50% without a significant decrease in plant growth. From FIG. 5 it can also be seen that while the addition of PA to the nutrient solution increased plant growth at all of the nutrient levels, the effect of PA was much greater at the relatively lower levels of nutrients. Specifically, an increase in plant growth of about 168% was noted when PA was added to a 25% Nutrient solution, and an increase of about 29% was noted when PA was added to a 100% Nutrient solution.

The foregoing specification and the Examples are intended to illustrate the present invention, but are not to be taken as limiting. Still other variations within the spirit and scope of this invention are possible and will readily present themselves to those skilled in the art.

We claim:

1. A composition, suitable for the promotion of plant growth, and comprising a mixture of
   a water-soluble, non-aromatic poly(organic acid) which is a poly(amino acid) of the group consisting of poly(aspartic acid), poly(glutamic acid), poly(glycine), poly(lysine), a copolymer of cysteine and glutamic acid, and a terpolymer of cysteine, glutamic acid and aspartic acid, said poly(amino acid) having at least about 15 repeating organic acid mers and a molecular size larger than 1,500 Daltons and
   a fertilizer for said plant.

2. The composition in accordance with claim 1 wherein the poly(amino acid) is poly(aspartic acid).

3. The composition in accordance with claim 1 wherein the poly(amino acid) is poly(aspartic acid) having a molecular size in the range of about 3,000 to about 28,000 Daltons.

4. The composition in accordance with claim 1 wherein the poly(amino acid) is poly(aspartic acid) having a molecular size in the range of about 3,000 to about 5,000 Daltons.

5. The composition in accordance with claim 1 wherein the poly(amino acid) is poly(glutamic acid).

6. The composition in accordance with claim 1 wherein the poly(amino acid) is poly(glutamic acid) having a molecular size in the range of about 4,000 to about 14,000 Daltons.

7. The composition in accordance with claim 1 wherein the poly(amino acid) is poly(glycine).

8. The composition in accordance with claim 1 wherein the poly(amino acid) is poly(glycine) having a molecular size in the range of more than 1,500 to about 7,000 Daltons.

9. The composition in accordance with claim 1 wherein the poly(amino acid) is poly(lysine).

10. The composition in accordance with claim 1 wherein the poly(amino acid) is poly(lysine) having a molecular size in the range of about 2,000 to about 7,000 Daltons.

11. A composition, suitable for the promotion of plant growth, which comprises a fertilizer for said plant; and a non-chelating, water-soluble, non-aromatic poly(organic acid) which is a poly(amino acid) of the group consisting of poly(aspartic acid), poly(glutamic acid), poly(glycine), poly(lysine), a copolymer of cysteine and glutamic acid, and a terpolymer of cysteine, glutamic acid and aspartic acid, said poly(amino acid) having a molecular size larger than that which can be absorbed by said plant.

12. The composition in accordance with claim 11 wherein said poly(organic acid) has a molecular size not larger than about 100,000 Daltons.

13. The composition in accordance with claim 11 wherein said poly(organic acid) has a molecular size in the range of about 2,000 to about 30,000 Daltons.

14. A method for promoting plant growth which comprises supplying to the plant a growth promoting amount of a water-soluble poly(organic acid) which is a poly(amino acid) of the group consisting of poly(aspartic acid), poly(glutamic acid), poly(glycine), poly(lysine), a copolymer of cysteine and glutamic acid, and a terpolymer of cysteine, glutamic acid and aspartic acid, said poly(amino acid) having a molecular size larger than 1,500 Daltons together with plant nutrients.

15. The method in accordance with claim 14 wherein said growth promoting amount is in the range of about 2 to about 500 ounces of the polymeric organic acid per acre.

16. The method in accordance with claim 14 wherein the growth promoting amount of said polymeric organic acid is provided as an aqueous solution containing at least about 10 parts per billion by weight of the polymeric organic acid.

17. The method in accordance with claim 14 wherein the growth promoting amount of said polymeric organic acid is provided as an aqueous solution containing about 0.1 to about 1,000 parts per million by weight of the polymeric organic acid.

18. The method in accordance with claim 17 wherein the polymeric organic acid is poly(aspartic acid).

19. The method in accordance with claim 14 wherein the polymeric organic acid is a copolymer of cysteine and glutamic acid.

20. The method in accordance with claim 14 wherein the polymeric organic acid is a terpolymer of cysteine, glutamic acid and aspartic acid.

* * * * *